United States Patent [19]

Leuchtenberger et al.

[11] Patent Number: 4,782,020

[45] Date of Patent: Nov. 1, 1988

[54] PROCESS FOR THE CONTINUOUS ENZYMATIC CONVERSION OF ALPHA-HYDROCARBOXYLIC ACIDS INTO THE CORRESPONDING OPTICALLY ACTIVE ALPHA-AMINOCARBOXYLIC ACIDS

[75] Inventors: Wolfgang Leuchtenberger, Bruchköbel; Christian Wandrey, Jülich; Maria-Regina Kula, Wolfenbüttel, all of Fed. Rep. of Germany

[73] Assignee: Degussa Aktiengesellschaft, Frankfurt, Fed. Rep. of Germany

[21] Appl. No.: 83,882

[22] Filed: Aug. 10, 1987

Related U.S. Application Data

[63] Continuation of Ser. No. 583,857, Feb. 27, 1984, abandoned.

[30] Foreign Application Priority Data

Mar. 1, 1983 [DE] Fed. Rep. of Germany ....... 3307094

[51] Int. Cl.$^4$ .................. C12Q 1/32; C12P 13/04; C12P 13/12; C12P 13/06
[52] U.S. Cl. ...................................... 435/106; 435/26; 435/113; 435/115; 435/111; 435/288; 435/813
[58] Field of Search ................. 435/26, 106, 113, 115, 435/116, 288, 813

[56] References Cited

U.S. PATENT DOCUMENTS

| | | | |
|---|---|---|---|
| 3,183,170 | 5/1965 | Kital et al. | 435/116 |
| 3,964,970 | 6/1976 | Dinelli et al. | 435/116 |
| 4,071,405 | 1/1978 | Seda et al. | 435/113 |
| 4,304,858 | 12/1981 | Wandrey et al. | 435/116 |
| 4,326,031 | 4/1982 | Wandrey et al. | 435/288 |

OTHER PUBLICATIONS

Mosbach, K. and P. O. Larsson "Immobilized Cofactors and Cofactor Fragments in General Ligand Affinity Chromatography" *Enzyme Eng.* III (Plenum, NY) 1975, pp. 291–298.

The Merck Index 10th Ed. (1983), Merck & Co., Inc., N.J., p. 6196, entry 6194.

Neilands, J. B., 1955, Methods in Enzyndogy, vol. I, pp. 449–454, Academic Press.

*Primary Examiner*—Charles F. Warren
*Assistant Examiner*—Elizabeth A. Hanley
*Attorney, Agent, or Firm*—Cushman, Darby & Cushman

[57] ABSTRACT

α-Hydroxycarboxylic acids are continuously converted into the corresponding optically active α-aminocarboxylic acids. The conversion is carried out in a membrane reactor in the presence of nicotinamide-adenine dinucleotide increased in molecular weight by bonding to a water soluble high molecular weight material, a dehydrogenase specific for the α-hydroxycarboxylic acid, a dehydrogenase specific for the corresponding α-amino-carboxylic acid and ammonium ions. There is continuously supplied to the membrane reactor an aqueous solution of the α-hydroxycarboxylic acid to be reacted, a substantially lesser amount of the corresponding α-ketocarboxy lic acid, and an amount of ammonium ion at least equivalent to the α-hydroxycarboxylic acid to be reacted. There is maintained over the membrane a difference in pressure 1 and 15 bar. Behind the membrane, there is continuously drawn off a filtrate stream containing the α-aminocarboxylic acid formed.

15 Claims, No Drawings

PROCESS FOR THE CONTINUOUS ENZYMATIC CONVERSION OF ALPHA-HYDROCARBOXYLIC ACIDS INTO THE CORRESPONDING OPTICALLY ACTIVE ALPHA-AMINOCARBOXYLIC ACIDS

This is a continuation of application Ser. No. 583,857, filed Feb. 27, 1984, which was abandoned upon the filing hereof.

BACKGROUND OF THE INVENTION

The invention is directed to a process for the continuous enzymatic conversion of α-hydroxycarboxylic acids into the corresponding optically active α-aminocarboxylic acids in an enzyme reactor in the presence of nicotinamide-adenine-dinucleotide ($NAD^+$/NADH), of increased molecular weight through bonding to a water soluble high molecular weight material, a dehydrogenase specific for the α-hydroxy-carboxylic acid employed, a dehydrogenase specific for the corresponding α-amino acid and ammonium ions.

There is already known a process for the continuous production of alanine from a lactate in an enzyme reactor in the presence of a nicotinamide-adenine-dinucleotide ($NAD^+$/NADH) of increased molecular weight through bonding to a water soluble dextran, lactate dehydrogenase, alanine-dehydrogenase and ammonium ions (K. Mosbach and P. O. Larsson in Enzyme Engineering BIII, pages 291 to 298). Our own experiments, however, have shown that this known process cannot be carried out continuously over a long period of time because the conversion to alanine after a relatively short period of time falls off sharply until finally the conversion comes to a complete stop and no more alanine is formed.

SUMMARY OF THE INVENTION

The process of the invention comprises employing a membrane reactor equipped with an ultrafiltration membrane having a nominal exclusion limit of 2,000 to 50,000 which contains an aqueous solution of 0.1 to 10 mmol/l of $NAD^+$/NADH bound to a polyethylene glycol having an average molecular weight between 500 and 50,000, the dehydrogenase specific for the α-hydroxy-carboxylic acid employed and the dehydrogenase specific for the α-aminocarboxylic acid formed, continuously supplying an aqueous solution of the α-hydroxycarboxylic acid to be converted in a concentration corresponding to 25 to 100% of the maximum amount soluble and the α-ketocarboxylic acid corresponding to the α-hydroxycarboxylic acid in a concentration between 1 and 10 $k_m$ based on the aminocarboxylic acid-dehydrogenase employed and an amount of ammonium ion at least equimolar to the amount of α-hydroxycarboxylic acid employed, maintaining a pressure difference over the membrane between 0.1 and 15 bar and continuously drawing off behind the membrane a filtrate stream containing the α-aminocarboxylic acid formed.

First the process of the invention permits the continuous conversion of α-hydroxycarboxylic acids over a long period of time into the corresponding optically active α-amino-carboxylic acids. The procedure essential for this consists of (or consists essentially of) supplying continuously to the membrane reactor not only the reacting α-hydroxycarboxylic acid but also in a substantially lesser amount compared to it of the corresponding α-ketocarboxylic acid. It is possible with the help of this procedure to continuously convert the α-hydroxycarboxylic acid employed, and with high space-time-yields, into the corresponding optically active α-aminocarboxylic acid and so these α-aminocarboxylic acid are produced economically.

There is used as reaction vessel a membrane reactor equipped with an ultrafiltration membrane, which membrane serves to retain in the reactor the enzyme employed and the coenzyme necessary for the conversion, but allows the lower molecular weight product and some of the unreacted substrate to pass through. The membrane reactor can be built as a so-called flat membrane reactor. With this type of reactor, for example, it is a matter of a flat cylindrical vessel on which there is placed a cover made tight by means of an O-ring. The planar, relatively expand flat membrane is stretched, together with the O-ring. The substrate stream is supplied through a metering pump to the reaction space below the membrane, which reaction space suitably is equipped with a stirring device, e.g., a magnetic stirrer. The filtrate stream containing the product leaves the reaction space through the membrane and a plate over it which is provided which bores arranged for the purpose of avoiding mechanical stress and the filtrate stream is drawn out of the cover. A so-called hollow fiber membrane reactor in which the ultrafiltration membrane, is a hollow fiber bundle (a so-called hollow fiber module) is advantageous because of the geometric arrangement allows high Reynolds numbers of the fluid parallel to the membrane and accordingly lower coatings of the membrane with enzyme proteins. For example, in this type of reactor, it is a matter of a type of loop reactor which consists of (or consists essentially of) a reaction container, a circulation pump, and the hollow-fiber-module. The substrate stream is supplied to the reaction container by means of a metering pump. The reaction mixture is circulated, whereby the circulating stream in relation to the substrate stream is at least about 100:1, in order to hold the coating of the hollow fiber membranes with enzyme protein as small as possible. The filtrate stream containing the product passes through the hollow fiber membranes and is collected behind this and drawn off. There are used for the process of the invention membranes which have a nominal exclusion limit of 2,000 to 50,000. Suitable materials for the membranes, for example, are acetyl cellulose, polyamides (e.g., nylon), polysulfones, or modified polyvinyl alcohol.

The membrane reactor contains an aqueous solution of 0.1 to 10 mmole/l of $NAD^+$/NADH present and bonded to a polyethylene glycol having an average molecular weight between 500 and 50,000, preferably between 1,500 and 20,000, a dehydrogenase specific for the α-hydroxy-caroxylic acid employed and a dehydrogenase specific for the α-aminocarboxylic acid to be formed.

The $NAD^+$/NADH having an increased molecular weight through bonding to the polyethylene glycol required as coenzyme, must still be water soluble in order to allow a homogeneous catalysis. However, on the other hand, it must be held back safely by the membrane together with the enzyme employed. For example, in German Patent No. 2841414, there is fully described the production of $NAD^+$/NADH of increased molecular weight. The entire disclosure of German patent No. 2841414 is hereby incorporated by reference and relied upon.

For this purpose, for example, the conenzyme in its oxidized form is first reacted with ethyleneimine to form the N(1)-aminoethyl derivative which in turn with the help of the carbodimide method [Cuatrecanas, J. Biol. Chem., Vol. 245, page 3059 (1970)] is coupled to a carboxylated polyethylene glycol, whose polyoxyethylene chain has an average molecular weight between 500 and 50,000, preferably between 15,000 and 20,000. The coupling product obtained is then reduced to the corresponding NADH derivative, converted by a Dimroth rearrangement into the N(6) derivative and in a given case again oxidized to the corresponding $NAD^+$ derivative. The coenzyme of increased in molecular weight is employed in such an amount that the concentration of $NAD^+$/NADH is 0.1 to 10 mmole/l, preferably 1 to 7 mmole/l.

The membrane reactor is continuously supplied with an aqueous solution of the α-hydroxycarboxylic acid to be reacted in a concentration corresponding to 25 to 100% of the maximum amount soluble. Fundamentally, it is naturally possible to employ a pure enantiomer of the α-hydrocarboxylic acid, thus either the L-form or the D-form and to have present in the membrane reactor a dehydrogenase specific for the enantiomer employed.

However, it is much more advantageous to employ the α-hydroxy-carboxylic acid as a racemate. Then in reference to the dehydrogenase, there are three possibilities. There can be employed a dehydrogenase which is specific only for one of the enantiomers. In this case, there always remains the other enantiomer unchanged and it leaves the membrane reactor with the filtrate stream, from which it can be recovered. Or there can be employed a mixture of dehydrogenases, one specific for the L-enantiomer and the other specific for the D-enantiomer. In this case then, both enantiomers are finally converted into the desired α-aminocarboxylic acid. The same goal is reached, however, if there is employed only one of the dehydrogenases specific for the L-enantiomer or the D-enantiomer, but there is present additionally in the membrane reactor the racemase specific for the α-hydroxycarboxylic acid employed.

Furthermore, there is continuously supplied to the membrane reactor an α-ketocarboxylic acid corresponding to the α-hydroxycarboxylic acid in such an amount that its concentration in the reactor is between 1 and 10 $k_m$ based on the aminocarboxylic acid-dehydrogenase employed, Hereby, $k_m$ signifies the reciprocal value of the adsorption equilibrium constant for the α-keto-carboxylic acid in reference to the dehydrogenase employed which is specific for the α-aminocarboxylic acid to be formed.

The α-ketocarboxylic acid can either be added to the aqueous solution of the α-hydroxycarboxylic to be reacted or it is dosed in separately in the form of an aqueous solution which under some circumstances can be more advantageous because then the dosing can be regulated independently.

Furthermore, there is continuously supplied to the membrane reactor ammonium ions in an amount at least equimolar to the amount of α-hydroxycarboxylic acid to be reacted. However, an excess of ammonium ions up to 3 times molar is not disturbing to the reaction. The supply of the ammonium ions is suitably carried out in such manner that there is added to the aqueous solution of the α-hydroxycarboxylic acid to be reacted a suitable ammonium salt, for example, ammonium formate, in the desired amount.

The dehydrogenase specific for the α-hydroxycarboxylic acid to be reacted is suitably employed in such an amount that in the equilibrium condition there is produced at least 50% of the equilibrium transformation obtainable in reference to the corresponding α-ketocarboxylic acid occurring as the intermediate product. The enzyme concentration necessary depends on the residence time and the starting concentration of the α-hydroxycarboxylic acid. With a residence time of 1 hour and a substate concentration of 100 mmole/l generally an α-hydroxycarboxylic acid-dehydrogenase activity of 10 U/ml is sufficient.

A racemase specific for the α-hydrocarboxylic acid to be employed is used additionally in some cases in such an amount that the racemization reaction runs with sufficient speed and is not the rate determining step of the entire reaction. Generally, there is sufficient for this purpose a racemase activity of 100 U/ml again if there is employed a residence time of 1 hour and a substate concentration of 100 mmole/l.

Finally, the dehydrogenase specific for the α-aminocarboxylic acid to be formed is employed suitably in such an amount that the ratio of $NAD^+$ to NADH established in the equilibrium condition is at least 5:1. For this purpose, there is employed up to 100 U/ml of the aminocarboxylic acid-dehydrogenase, in order to establish at a residence time of 1 hour and a substate concentration of 100 mmole/l at least 90% of the equilibrium conversion which is thermodynamically possible with the coupled reaction system.

There must be maintained over the membrane during the conversion a difference in pressure of 0.1 to 15 bar, preferably 0.2 to 3 bar, which is accomplished by using a correspondingly dimensioned metering pump for the substate solution supplied and in a given case by a butterfly valve in the filtrate stream behind the membrane. The pressure differential causes a filtrate stream to pass through the membrane with the desired speed. The absolute pressure on the pressure side of the membrane should suitably be regulated so that even with vigorous stirring or recirculating in the reaction space before the membrane for the production of a vigorous turbulence along the membrane and therewith to avoid a coating of the membrane with the enzymes or the coenzyme of increased molecular weight at no place is the pressure reduced to such an extent that there occurs a degassing of the reaction mixture on the pressure side.

The membrane reactor is held at a temperature between 25° and 50° C. customary for enzymatic conversions. The pH of the reaction mixture is held suitably in the range between 8 and 9.5 during the reaction.

In practice, at present there can only be produced according to the invention L-α-aminocarboxylic acids because until now D-aminoacid dehydrogenases are not available. However, moreover, the process of the invention is widely employed. For example, with the enzyme systems L- or D- or L- and D-lactate-dehydrogenase+L-alanine-dehydrogenase or L- or D-lactate-dehydrogenase+lactate racemase (E.C.5.1.2.1)+L-alanine-dehydrogenase, there can be converted lactic acid into L-alanine. With the enzyme system L- or D- or L- and D-2-hydroxy-4-methylpentanoic acid-dehydrogenase +L-leucine-dehydrogenase there can be converted 2-hydroxy-4-methylmercapto butyric acid into L-methionine, 2-hydroxy-3-methylbutyric acid into L-valine, 2-hydroxy-4-methylpentanoic acid into L-leucine or 2-hydroxy-3-methylpentanoic acid into L-isoleucine. With the enzyme system L- or D- or L- and D-lactate-dehydrogenase+L-phenylalanine-dehydrogenase, there can be converted phenyl lactic acid into L-phenylalanine. With the enzyme system L- or D- or L- and D-indolyl lactate-dehydrogenase+L-phenylanine-dehydrogenase, there can be converted indolyl lactic acid into L-tryptophane.

Unless otherwise indicated, all parts and percentages are by weight.

The process can comprise, consist essentially of, or consist of the stated steps with the recited materials.

DETAILED DESCRIPTION

The process of the invention is explained in more detail in the following examples.

EXAMPLE 1

A flat membrane reactor having a volume of 11.3 ml equipped with a magnetic stirrer and an ultrafiltration membrane having a diameter of 62 mm and a nominal exclusion limit of 5,000 (supplier, Amicon, Witten, Germany; Type YM5) was held at a temperature of 25° C. and for sterilization was rinsed for about 5 hours by means of an aqueous 70% ethanol solution held at a conveying speed of 11.3 ml per hour by means of a metering pump. Subsequently, the aqueous alcohol solution was displaced during about a further 5 hours by distilled water. Then at a conveying speed of 9.3 ml per hour for about 5 hours, there was supplied via a sterile filter (0.2 $\mu$m) filtered substrate solution which contained 243 mmole/l of DL-lactic acid in the form of the sodium salt and 486 mmole/l of ammonium formate and was adjusted to pH 9 with aqueous sodium hydroxide. Simultaneously, there was supplied with a second metering pump via the same sterile filter at a conveying speed of 2 ml per hour for about 5 hours a pyruvate solution which contained 11.3 mmole/l of pyruvic acid in the form of its sodium salt and was adjusted with aqueous sodium hydroxide to pH 9. There resulted through this before the reaction was started in the reactor a starting concentration in the reactor of 200 mmole/l of DL-lactate, 400 mmole/l of ammonium formate, and 2 mmole/l of pyruvate. Then, there was injected into the substrate dosing via a Septum before the sterile filter an enzyme/coenzyme-mixture of the type that there was present in the reactor a concentration of 1.32 mmole/l NAD+/NADH bound to a polyethylene glycol having an average molecular weight of 20,000, as well as a L-lactatedehydrogenase activity of 60.5 U/ml (measured with 0.2 mole/l of DL-lactate, 12 mmole/l of NAD+, 25° C., pH 9), as well as an L-alaninedehydrogenase-activity of 178.6 U/ml (measured with 2 mmole/l of pyruvate, 2 mmole/l NADH, 400 mmole/l of ammonium formate, 25° C., pH 9).

The reactor was operated continuously over 6 days with a residence time of 60 minutes at 25° C. and pH 9. During the entire time of operation, the pressure difference over the membrane was about 1.7 bar. The maximum initial conversion was 80%, and this fell in the course of 6 days to 60% (conversion based on the L-enantiomer in the substrate). The maximum space-time-yield was 1.92 mole/(l×d) or 171 g/(l×d). Withn an operating time of 6 days, there were obtained 10.1 grams or 113 mmoles of L-alanine. The enzymatically active coenzyme concentration fell in the course of 6 days from 1.32 mmole/l to 0.49 mmole/l.

Per mole of coenzyme (used up), there were formed 12,000 moles of product. This corresponds to a need of 615 mg NAD+ (native)/kg product.

EXAMPLE 2

A flat membrane reactor having a volume of 10.0 ml equipped with a magnetic stirrer and an untrafiltration membrane having a diameter of 62 mm and a nominal exclusion limit of 5,000 (supplier, Amicon, Witten, Germany, Type YM5) for sterilization was rinsed for about 2 hours with 0.05% aqueous peracetic acid solution at a conveying speed of 20 ml/hour regulated by means of a metering pump. Subsequently, the sterilization solution was displaced during about a further 10 hours by distilled water. Then at a conveying speed at 10 ml/hour for 4 hours, there was supplied via a sterile filter (0.2 $\mu$m) substrate solution which contained 400 mmole/l of DL-2-hydroxy-4-methylmercapto-butyric acid ("DL-hydroxymethionine"), 800 mmole/l of ammonium formate and 1 mmole/l of 2-keto-4-methylmercaptobutyric acid and was adjusted to pH 8 with aqueous sodium hydroxide.

In a separate reactor (glass beaker), there was allowed to react over a period of 24 hours 25 ml of a like concentrated substarate solution which contained the enzyme L-leucine-dehydrogenase and L-2-hydroxy-4-methylpentanoic acid-dehydrogenase as well as coenzyme NADH bound to polyethylene glycol 20,000. Thereby, there were used ensyme and coenzyme concentrations which in the course of the 24 hours at least would reach a conversion that would be sought later in the continuous experiment.

This solution was then dosed into the flat membrane reactor with a conveying speed of 2.7 ml/hour. Then, there was further dosed in at the same conveying speed the above-stated substate solution.

Since the enzyme and the coenzyme could pass the sterile filter before the reactor but not the ultrafilter of the reactor arrangement itself, there resulted in the reactor a concentration of 1.42 mmole/l of coenzyme, as well as a L-2-hydroxy-4-methylpentanoic acid-dehydrogenase-activity of 4.0 U/ml (measured with 0.4 mole/l of DL-2-hydroxy-4-methylmercapto-butyric acid, 1 mmole/l of NADH, 800 mmole/l of ammonium formate, 25° C., pH 8), and an L-leucinedehydrogenase activity of 86.3 U/ml (measured with 2 mmole/l of 2-keto-4-methylmercapto-butyric acid, 1 mmole/l NADH, 800 mmole/l ammonium formate, 25° C., pH 8).

The reactor was operated continuously with a residence time of 3.7 hours at 25° C. and pH of 8 under the conditions mentioned over about 4.5 days. During this time of operation, the maximum difference in pressure over the membrane was about 3 bar. In the time of the experiment, there was attained a maximum conversion of 38.4%, which reduced in the course of 2.6 days to 36.4% (conversion based on the L-enantiomer in the substrate). The maximum space-time-yield was 0.5 mole/(l×d) or 74.3 g/(l×d). Inside an operating time of 4.34 days, there were obtained 3 grams of 20 mmoles of L-methionine. The enzymatically active coenzyme concentration fell in the course of 4.34 days from 1.42 mmoles/l to 1.25 mmoles/l.

Per mole of coenzyme (used up), there were formed 11,800 moles of product. This corresponds to a need of 378 mg NAD+ (native/kg product).

The entire disclosure of German priority application No. P.3307094.6 is hereby incorporated by reference.

What is claimed is:

1. In a process for the continuous enzymatic conversion of an α-hydroxycarboxylic acid into the corresponding optically active α-aminocarboxylic acid in an enzyme reactor in the presence of nicotinamide-adenine-dinucleotide (NAD+/NADH) of increased molecular weight through binding to a water soluble high molecular weight material, a dehydrogenase specific for the α-hydroxycarboxylic acid employed, a dehydrogenase specific for the α-aminocarboxylic acid to be formed, and ammonium ions the improvement comprising employing a membrane reactor equipped with an ultrafiltration membrane having a nominal exclusion limit of 2,000 to 50,000 which contains an aqueous solution of 0.1 to 10 mmole/l of NAD+/NADH bound to a polyethylene glycol having an average molecular weight between 500 and 50,000, the dehydrogenase specific for the α-hydroxycarboxylic acid employed and the dehydrogenase specific for the α-aminocarboxylic acid to be formed, continuously supplying an aqueous solution of the α-hydroxycarboxylic acid to be reacted in a concentration of 25 to 100% of the maximum amount soluble and of the α-ketocarboxylic acid corresponding to that α-hydroxycarboxylic acid in a concentration between 1 and 10 $k_m$, based on the aminocarboxylic acid-dehydrogenase employed and an amount of ammonium ion at least equimolar to the amount of α-hydroxycarboxylic acid to be reacted, maintaining a difference in pressure over the membrane between 0.1 and 15 bar and continuously drawing off behind the membrane a filtrate stream containing the α-aminocarboxylic acid formed.

2. A process according to claim 1 wherein there is employed the α-hydroxycarboxylic acid in the form of the racemate and there is employed a mixture of the dehydrogenase specific for the L-enantiomer and a dehydrogenase specific for the D-enantiomer.

3. A process according to claim 1 wherein the α-hydroxycarboxylic acid is employed in the form of a racemate, there is used only a dehydrogenase specific for the L-enantiomer or a dehydrogenase specific for the D-enantiomer, and the reaction is carried out in the simultaneous presence of a racemase specific for the α-hydroxycarboxylic acid.

4. A process according to claim 3 wherein there is employed a dehydrogenase specific for the L-enantiomer.

5. A process according to claim 1 wherein the polyethylene glycol has an average molecular weight between 1,500 and 20,000.

6. A process according to claim 5 wherein the concentration of NAD+/NADH is 1 to 7 mmoles/l.

7. A process according to claim 6 wherein the polyethylene glycol has a molecular weight of 20,000.

8. A process according to claim 7 wherein the pH is between 8 and 9.5.

9. A process according to claim 8 wherein the ratio of NAD+ to NADH is at least 5:1.

10. A process according to claim 9 wherein the α-hydroxycarboxylic acid employed is lactic acid or 2-hydroxy-4-methylmercaptobutyric acid.

11. A process according to claim 1 wherein the pH is 8 to 9.5.

12. A process according to claim 11 wherein the α-hydroxycarboxylic acid is lactic acid, 2-hydroxy-4-methylmercapto-butyric acid, 2-hydroxy-3-methylbutyric acid, 2-hydroxy-4-methyl-pentanoic acid, 2-hydroxy-3-methyl-pentanoic acid, phenyllactic acid, or indolyllactic acid.

13. A process according to claim 1 wherein the α-hydroxycarboxylic acid is lactic acid or 2-hydroxy-4-methylmercapto butyric acid.

14. A process according to claim 1 wherein the improvement consists of the steps recited.

15. A process according to claim 1 wherein improvement consists essentially of the steps recited.

* * * * *